United States Patent [19]
Sontvedt

[11] Patent Number: 5,250,807
[45] Date of Patent: Oct. 5, 1993

[54] SAND DETECTOR

[75] Inventor: Terje Sontvedt, Gjettum, Norway

[73] Assignee: Norsk Hydro a.s., Oslo, Norway

[21] Appl. No.: 778,925

[22] PCT Filed: Jul. 6, 1990

[86] PCT No.: PCT/NO90/00112

§ 371 Date: Dec. 11, 1991

§ 102(e) Date: Dec. 11, 1991

[87] PCT Pub. No.: WO91/00991

PCT Pub. Date: Jan. 24, 1991

[30] Foreign Application Priority Data

Jul. 7, 1989 [NO] Norway ................. 892819

[51] Int. Cl.$^5$ .................. G01N 3/56; G01N 15/06
[52] U.S. Cl. ............................. 250/303; 250/260
[58] Field of Search ........................ 250/303, 260

[56] References Cited

U.S. PATENT DOCUMENTS

T913,010 8/1973 Arnold et al.
3,678,273 7/1972 Lewis
3,767,916 10/1973 Lewis
4,305,278 12/1981 Stewart et al.

FOREIGN PATENT DOCUMENTS 0016639 10/1980 European Pat. Off.
0317339 5/1989 European Pat. Off.
2425113 12/1975 Fed. Rep. of Germany ...... 250/303
0127854 7/1959 U.S.S.R. ......................... 250/303

Primary Examiner—Paul M. Dzierzynski
Assistant Examiner—Richard Hanig
Attorney, Agent, or Firm—Wenderoth, Lind & Ponack

[57] ABSTRACT

A method of measuring or detecting an unknown distribution and content of solid material in a flow of liquid and gas is achieved without any calibration. One or several activated probes or specimens emitting radiation are used. The radiation is measured by a detector on the outside of the flow pipe. Each probe emits radiation only to one detector. The probes are mounted apart both lengthwise and across the pipe section. The probes are mounted at an angle α to the fluid flow, 20° <α<60°. Without any signal analyses, the probes will register whether the fluid flow contains solid material if the thickness of the probes is reduced 0.1 %. The particle content is calculated with a 0.25% thickness reduction. The amount of the particles impinging the probes can be calculated.

9 Claims, 10 Drawing Sheets

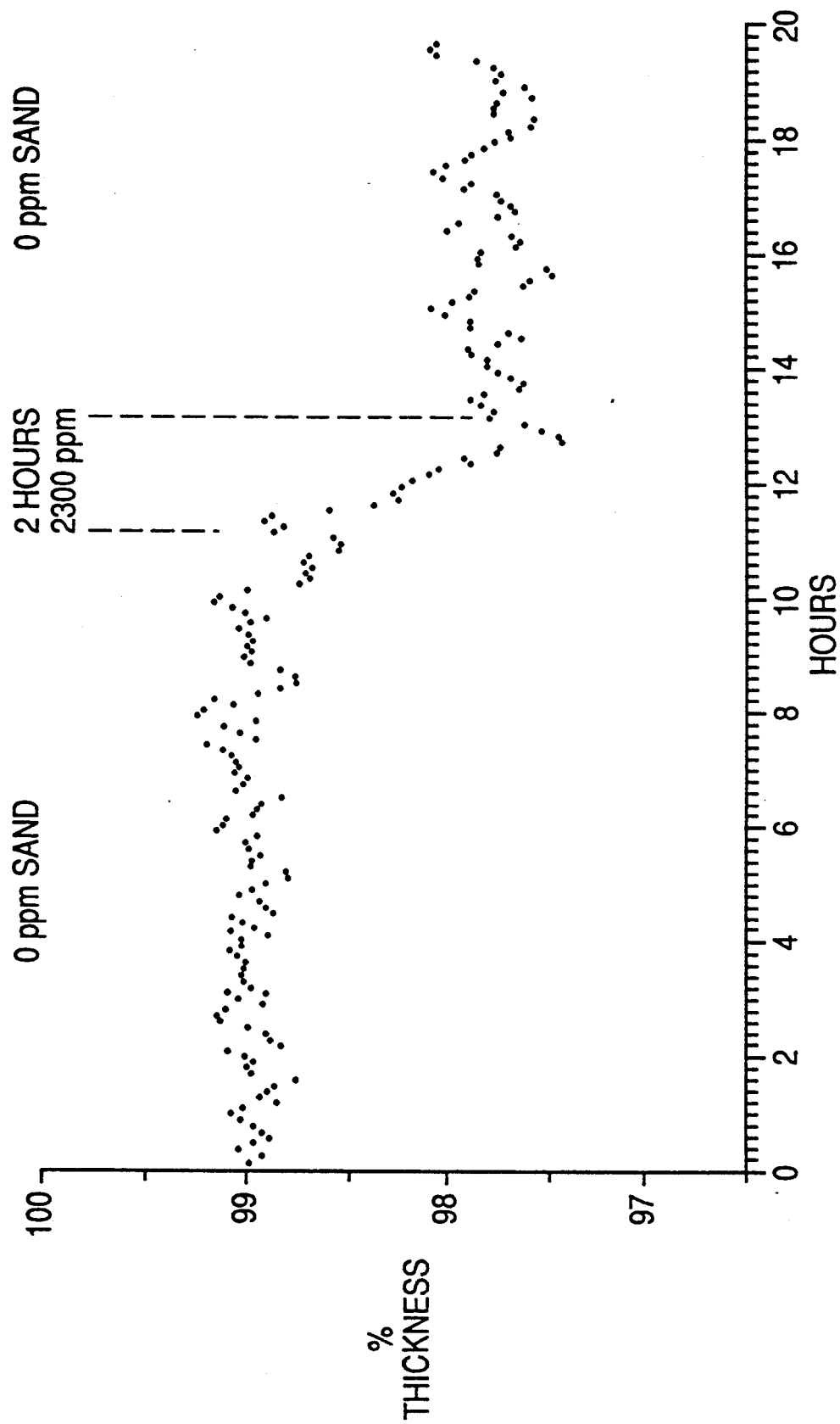

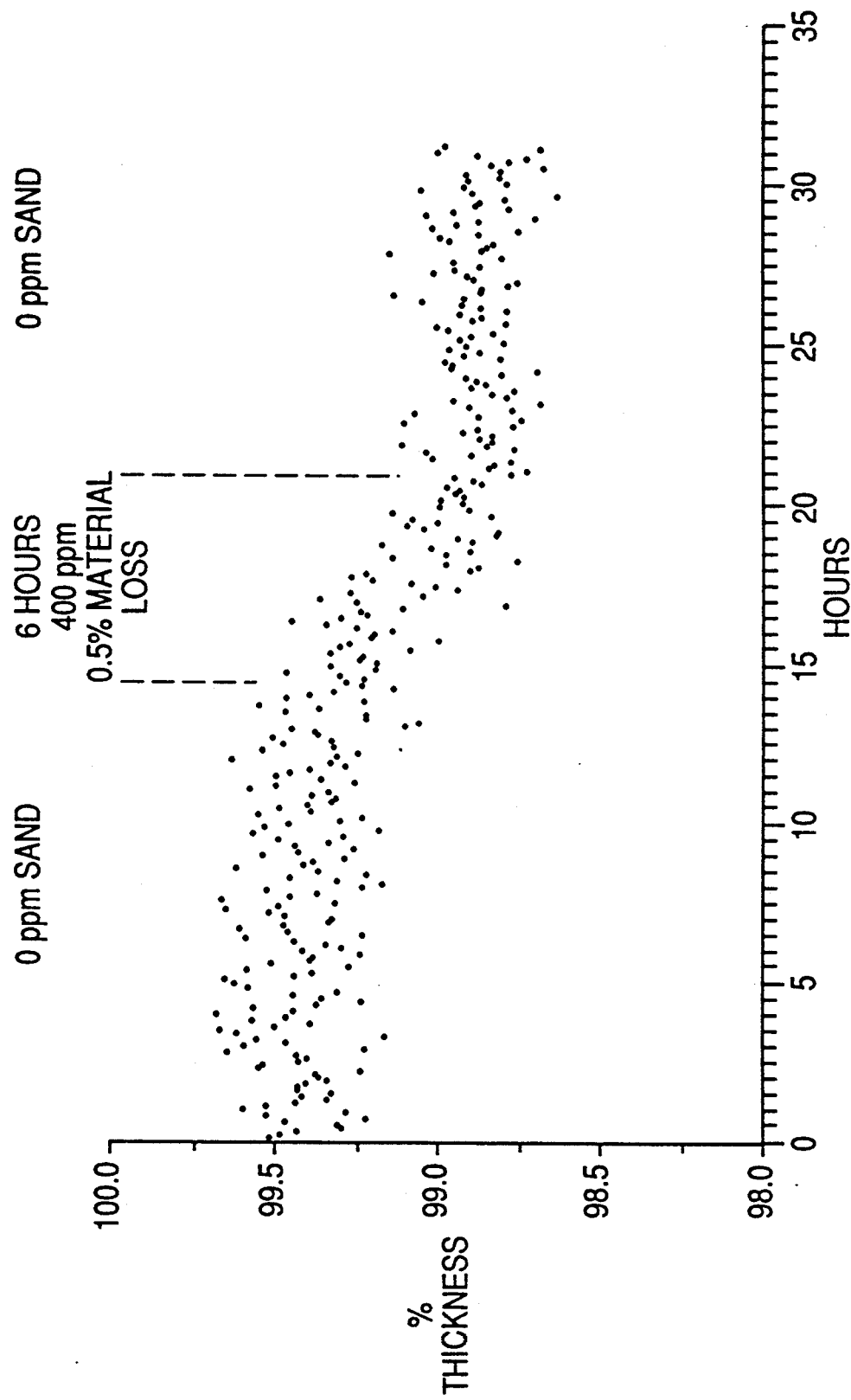

SAND DETECTOR

BACKGROUND OF THE INVENTION

The invention relates to a method of measuring the amount of abrasive material in a fluid flow of liquid and/or gas. The method can, for example, be employed to supervise the production rate of sand in an oil and/or gas production well.

Production of oil and gas often results in that the produced oil and gas contains sand. For production wells in a sandstone reservoir without a sand controlling system it is assumed that more than 25 ppm of quartz particles with diameter of 1-1000 μm may be produced. If a sand controlling system is employed, sand production will be approximately 25 ppm with a diameter of 0-100 μm. Sand production cannot only cause severe erosion of the production equipment, but large quantities of sand can also be accumulated in the equipment and result in production break down. If the production of said is measured reliably, the production rate can be adjusted and the problems relating to erosion and accumulation of sand can be reduced. The maximum production rate without producing sand can thus be established. Therefore, there is a need to monitor small/medium said production rates with either small particles (applying gravel packs) or with a full spectrum of the particle size. Monitoring should preferably be applied on each individual well. There are also various other applications where continuous supervision is important when there is danger of contamination of abrasive materials in fluid flows.

Different systems have been used or suggested for monitoring or detecting said content in a fluid well. One system to employ in a fluid flow to determine abrasion caused by sand is an erosion probe. Sand can erode, for example, a thin, hollow-walled probe which is mounted in the fluid flow. A pressure difference between the fluid flow and a reference point will activate an alarm. Therefore, there will be a considerable time delay before this probe detects sand, and it will not give continuous monitoring of the sand content in the fluid flow or of the sand production rate.

There are also known different acoustic probes that either can be clamped on the outside of a pipe wall or mounted inside the pipe. This probe can detect said production in either a gas or a liquid flow. The ability to distinguish between sand noise and other noise is not satisfactory in intermittent or annular/mist fluid flows. Calibration of the acoustic probe has to be performed with actual production parameters and by injection of said. The calibration will change when the production rate or other sources of noise are varied.

Small particles (0-0.5 mm dia.) produce acoustic energy too low to discriminate between particle- and flow noise. One such acoustic probe is described in NO Patent No. 140,838.

From U.S. Pat. No. 3,678,273, 3,767,916 and EP Patent No. 0 317 339 disclose various methods for measuring erosion caused by abrasive fluid. Common for these known methods is that a detector coated with a radioactive material is positioned in a fluid flow, for example an oil slurry. The detector is activated by radiation from the radioactive coating due to a thickness reduction caused by the abrasive fluid, the detector is in contact with a control and monitoring unit on the outside of the pipe. The particle concentration of the flow is determined by determining the particle in a concentration of an equivalent flow of known composition which causes the measured reduction of radiation emission when it contacts an equivalent material at the measured flow velocity.

The particle concentration in the flow can thus be estimated. The detector is mounted in the flow and will be an obstruction to the flow. The detector will not be able to detect small particles because these particles will follow the flow and pass around the obstruction. This detector can therefore not be used in a high pressure hydrocarbon pipe where it is impossible to predict the sand distribution. The accuracy and how the particle content is measured are not discussed. The method requires calibration and a uniform distribution of the abrasive particles.

SUMMARY OF THE INVENTION

The object of the present invention is to provide an improved method for continuous monitoring of the production rate of abrasive particles in a hydrocarbon well. It is important to be able to estimate the total mass of sand produced without having to calibrate the system. It is also an object of the invention to provide an accurate system which is sensitive to a low production rate and also be able to adjust the sensitivity of the probe to the necessary limits for an adequate control. The system has to tolerate a two phase flow and detect small particles.

These and other objects are achieved in accordance with the invention as described below and as defined by the claims.

By the present invention there is achieved a method to detect abrasive material in a production flow containing an unknown amount and distribution of particles, without having to calibrate the system. Several probes are activated and emit radiation to detectors at the outside of a pipe wall containing the flow. Each monitored probe emits signals only to one detector. The probes are positioned with spaces between each other, both in the longitudinal direction and in the circumferential direction. The probes are positioned at an angle $\alpha$ to the fluid flow, where $20° < \alpha < 60°$. Without any signal processing, the probes will register that the fluid flow contains particles if the thickness of the radioactive coating is reduced by 0.1%. The particle concentration is determined if the thickness of the coating is reduced by 0.25%.

The quantity Mg of particles impinging the probes can be determined by the following equation:

$$Mg = \frac{E \times A}{K \times F \times V^{2.62}} \times (kg)$$

wherein
  E = Reduction of probe thickness (mm)
  A = The pipe cross sectional area (m$^2$)
  K = material constant for the activated material
  F = Function of the flow density and mean diameter Dp (mm) of the solid particles in the reservoir;

$$F = \frac{Dp}{B \times \phi^{0.5}}$$

B = Constant for all gas/liquid ratios
  $\phi$ = Flow density (kg/m$^3$)
  V = Velocity of the flow (m/s).

BRIEF DESCRIPTION OF THE DRAWINGS

The invention will be explained in detail with reference to the enclosed drawings, wherein:

FIG. 9 is a graph illustrating the loss of material during two hours in a fluid flow containing 2300 ppm said; and FIG. 10 is a graph illustrating the loss of material during six hours in a fluid flow containing 400 ppm sand.

DETAILED DESCRIPTION OF THE INVENTION

A sand detector is based on measuring the loss of radioactive material. The measurement of material loss by a radioactive technique is based on irradiating a test piece with neutrons or other energy rich particles, thus forming radioactive isotopes in the test specimen. The radioactive isotopes will emit radioactivity and simultaneously be transformed to a new material. The intensity of the emitted radiation can be measured and will be directly proportional to the amount of material in the specimen. Because the test specimen corrodes or erodes when placed in an abrasive flow, the intensity will be reduced due to the material loss, and thus it will be possible to measure the corrosion or erosion very accurately.

The specimens used to measure the material loss can be made radioactive by thin coat activation or neutron activation. In both cases the specimens are irradiated with energy rich particles, thus forming radioactive isotopes in the material. The actual quantity of isotopes formed is less than 1 ppm. The material properties are not changed. Neutron activation implies neutrons with a deep penetration depth causing most of the irradiation to pass through the material. The activating profile has an almost constant activation level. It is therefore relatively easy to interpret the data because the loss of irradiation intensity is a direct expression of the weight loss of the specimen. When it is activated, it is important to form isotopes having a $\gamma$-energy large enough to reach the detector. It is also important to use isotopes with a half-life for continuous erosion/corrosion measurement over a period of several years.

An applicable isotope $Co^{60}$ is formed when steel is neutron activated, because almost all steels contain small amounts of Co. The $Co^{60}$ isotope has a $\gamma$-energy level of 1.17 MeV and 1.32 MeV and a half-life of 5.27 years. With this relatively long half-life one can perform erosion/corrosion measurements on process equipment for a period of 20–25 years without changing the specimens or penetrating the equipment.

However, during experiments there was used a stamped out circular 110 $\mu$m thick Inconell 600 steel folio which under irradiation mainly emitted the isotope $51_{Cr}$ and some $60_{Co}$. $51_{Cr}$ has a short half-life and a low $\gamma$-energy level (0.32 Mev).

Figure 1:
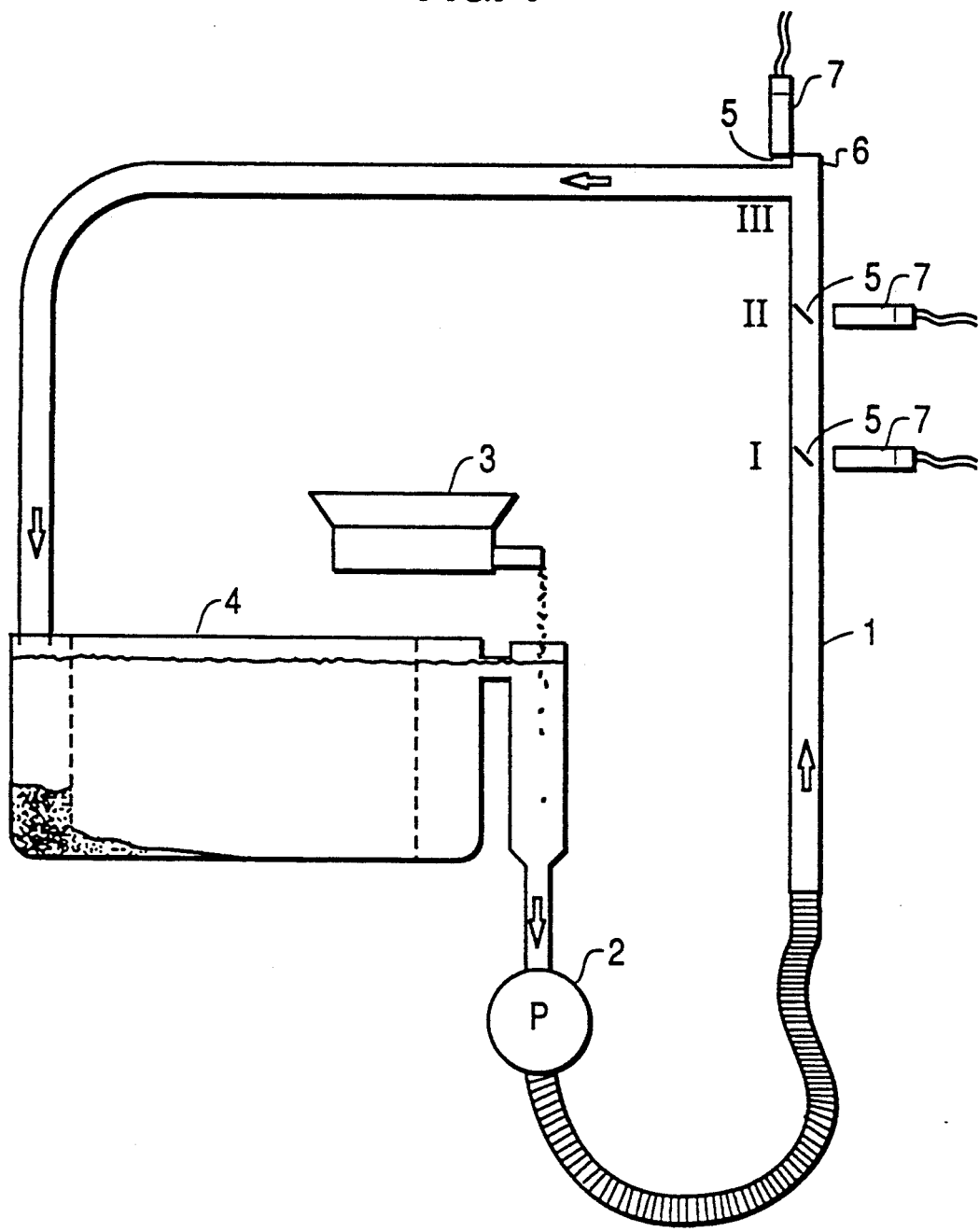
FIG. 1 is a schematic view illustrating a testing arrangement.

The experiments were performed by the testing arrangement shown in FIG. 1. It comprised a test section of steel including pipes 1 and 6, a pump 2 with variable capacity, a sand feeder 3 with variable feeding rate, and necessary tanks 4 for sand and water. In the first part of the test period the sand was fed continuously without recirculation. The sand grains were of medium size, approximately 0.50 mm. The flow velocity could be regulated from 1 to 6 m/s and the sand flow from 1 to 30,000 ppm. The largest sand concentration used in the tests was 5400 ppm.

Test specimens (i.e. probes) 5 were positioned as shown in the drawings. Three different locations of test specimens were used; i.e. one where the activated folio was positioned at the end of the pipe 6, one where the test piece was positioned in the vertical pipe 1 at an angle of 20° with respect to the direction of fluid flow, and one where the activated folio was mounted in the middle of the pipe. Such different locations are indicated in FIG. 1 as III, II, I, respectively. The test specimens 5 were mounted on movable axles or arms so the angle between the activated surface and the fluid flow could be adjusted and could be pushed/pulled within the pipe. The detectors are indicated at 7 in FIG. 1.

Figure 2:
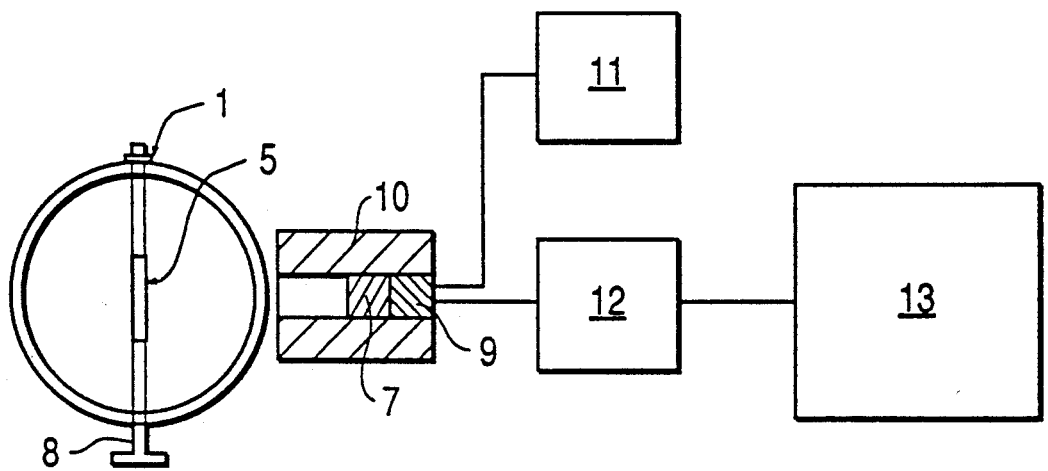
FIG. 2 is a schematic sectional view of the testing arrangement including a detector and an analyzer.

FIG. 2 is an enlarged section of the testing arrangement illustrated in FIG. 1. The fluid flow passes through the pipe 1. The activated test specimen 5 was mounted on a rotatable and movable arm 8. The detector 7 was positioned approximately 10 cm from the pipe. Increased distance from the pipe would require a stronger energy source because the irradiation intensity is reduced by the square of the distance. The thickness of the pipe wall can be larger if necessary, or one can use a concrete cover or isolation between the test specimen and the detector. However, the material between the test piece and the detector has to be constant and should not change over time. Gamma radiation from the surface of the test piece was picked up by a scintillation detector with NaI-crystals emitting light when radiated. The energy band of the light gave specific information of the radiation intensity from the surface of the test piece. The detector 7 was connected to a pre-amplifier 9 and was protected by a lead cover 10. Detector 7 also was connected to high voltage source 11, an amplifier 12 and an analyzer 13. Most of the experiments were performed with two of the movable test pieces positioned one after the other with a distance therebetween of 60 cm.

Several tests were performed to determine optimum conditions for the process of the invention.

Test 1

Figure 3:
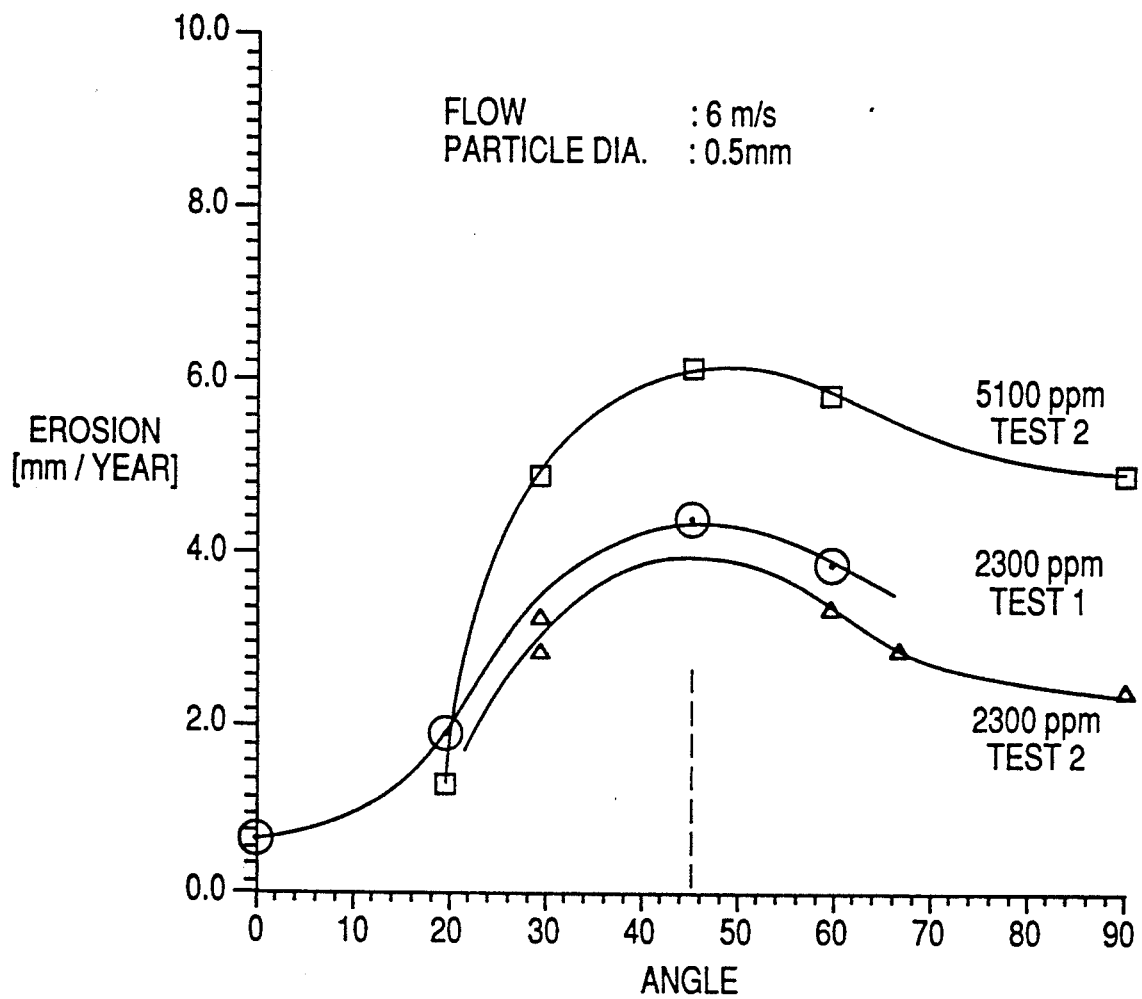
FIG. 3 is a graph showing erosion velocity as a function of angles of test specimens to flow, fluid flow velocity being 6 m/s.
Figure 4:
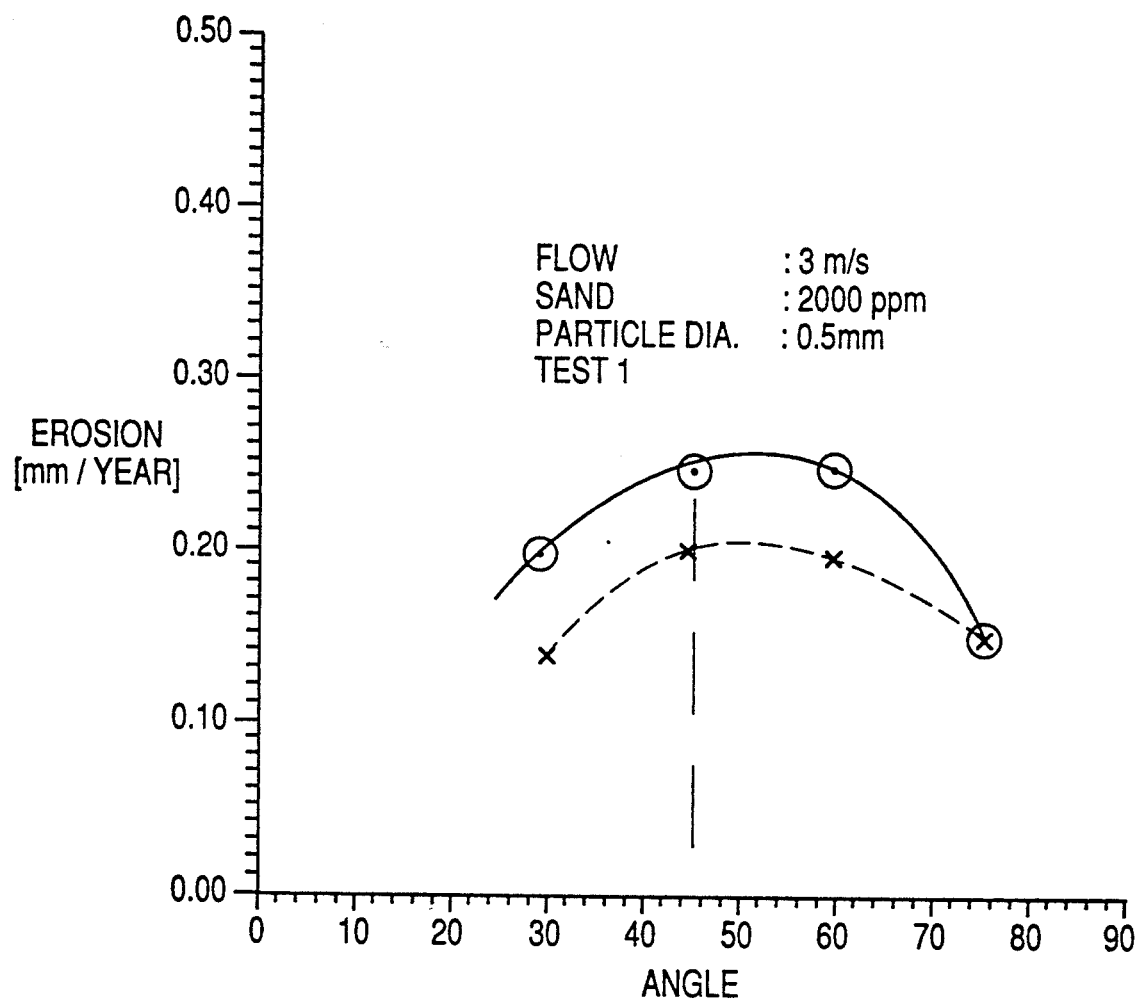
FIG. 4 is a graph showing the erosion velocity as a function of the test specimens angles to the flow, at a fluid flow velocity of 3 m/s.

Tests were carried out to examine the effect of the angle of the test specimens with respect to the fluid flow. Movable test specimens were used. FIG. 3 illustrates erosion velocity as a function of the angle of the test specimens, at a fluid velocity of 6 m/s and sand concentrations of 5100 ppm and 2300 ppm. The angle between the test specimens and the flow varied between 0° and 90° and the test specimens were located in the middle of the pipe. From FIG. 3 one can conclude that the erosion velocity increases when the angle is increased up to 45°, then decreases and reaches a minimum at 90°. In FIG. 4 the erosion velocity is illustrated with a reduced flow velocity of 3 m/s. The test results indicate that the maximum erosion rate is at approximately 50°, then decreases down to a minimum at 90° which is at a level below the results from the test when the velocity was 6 m/s. The dotted line in FIG. 4 indicates calculated values.

Test 2

Figure 5A:
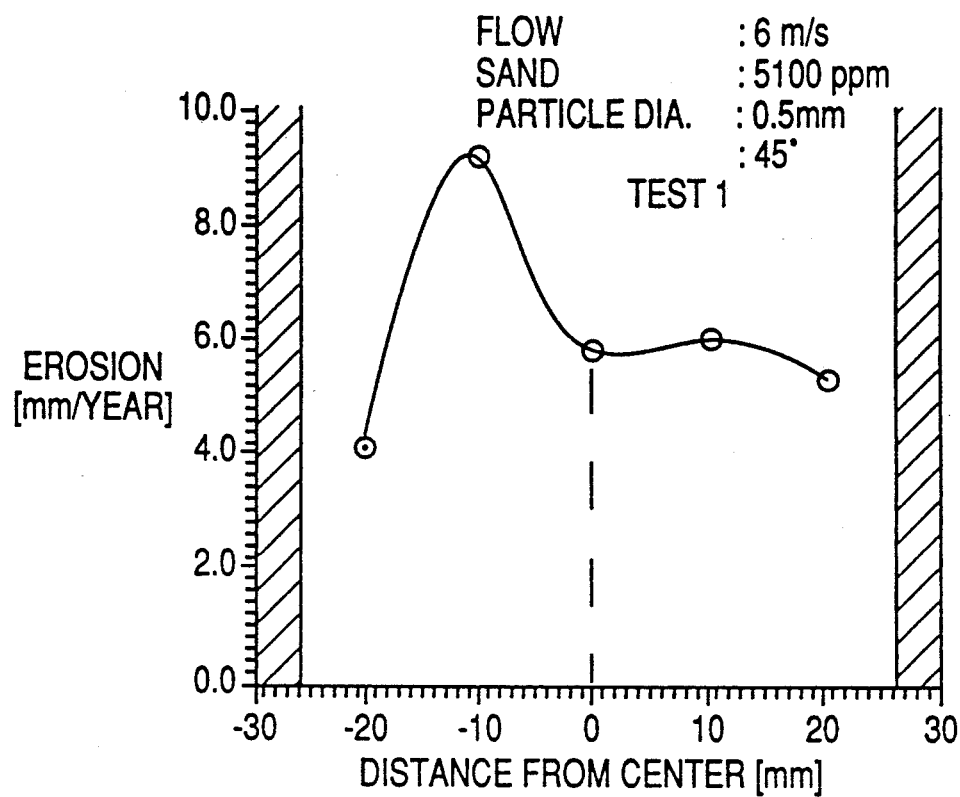
FIG. 5A is a graph showing the erosion velocity as a function of the distance from a test specimen to a center line of a test tube, with fluid flow velocity being 6 m/s.
Figure 5B:
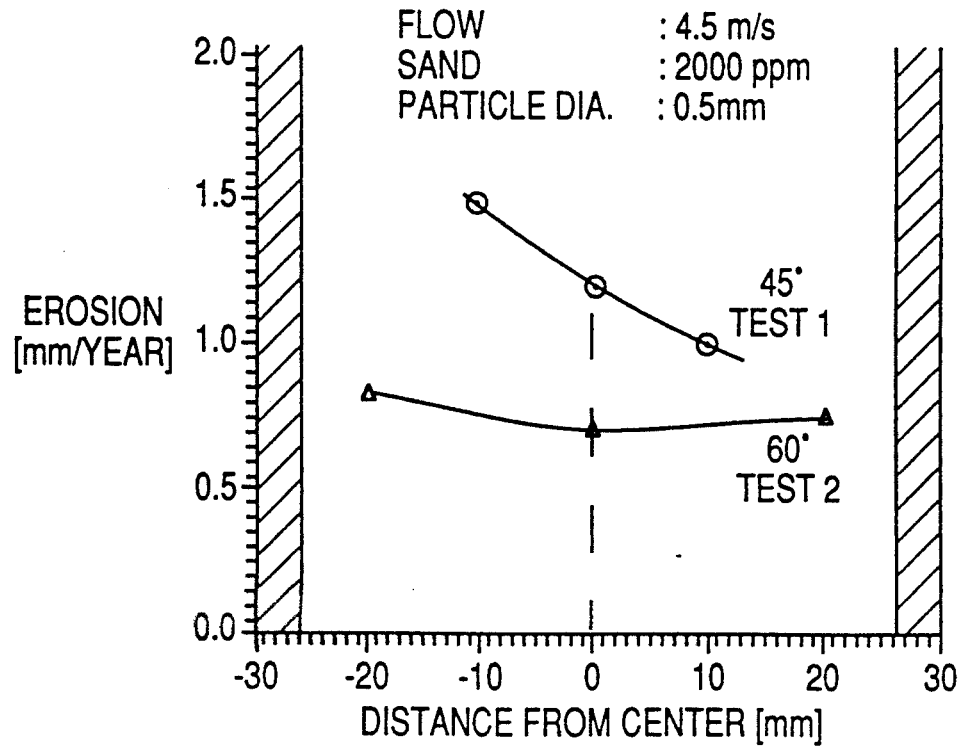
FIG. 5B is a graph similar to FIG. 5A, but with fluid flow velocity being 4.5 m/s.

In several tests the test specimens were moved backward and forward transversely to the flow direction to study the sand distribution within the cross section of the pipe. FIG. 5A illustrates the results from the conditions of test with a flow velocity of 6 m/s, an angle of 45°, sand concentration of 5100 ppm and sand grain size of 500 μm. The graph indicates a non-uniform distribution in the pipe. The inlet length was 2.5 m. FIG. 5B illustrates the same type of test as described above, but with a flow velocity of 4.5 m/s, a sand concentration of 2000 ppm and test specimen angles of 45° and 60° for specimens I and II. The sand distribution is non-uniform for specimen I with respect to the central axis in the pipe. The sand distribution is more uniformly distributed for specimen II. This indicates that specimen I which is mounted 60 cm in front of specimen II was located in a more homogeneous sand/water flow.

For location of the test specimen as shown in FIG. 1 the largest erosion on the specimen was measured in the center of the pipe and with an angle of 45° to the flow direction (test 1). The erosion of a flush mounted specimen 1 cm from the end of the T-shaped pipe was 60% of the erosion on test specimen III. Test specimen III mounted at the wall had an erosion 75% of test specimen I. This indicates that sand is concentrated in the center of the pipe.

Figure 6A:
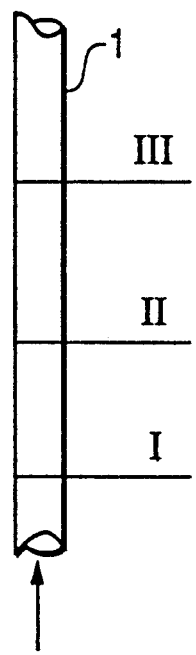
FIGS. 6A and 6B are schematic views illustrating the optimum location of three probes.
Figure 6B:
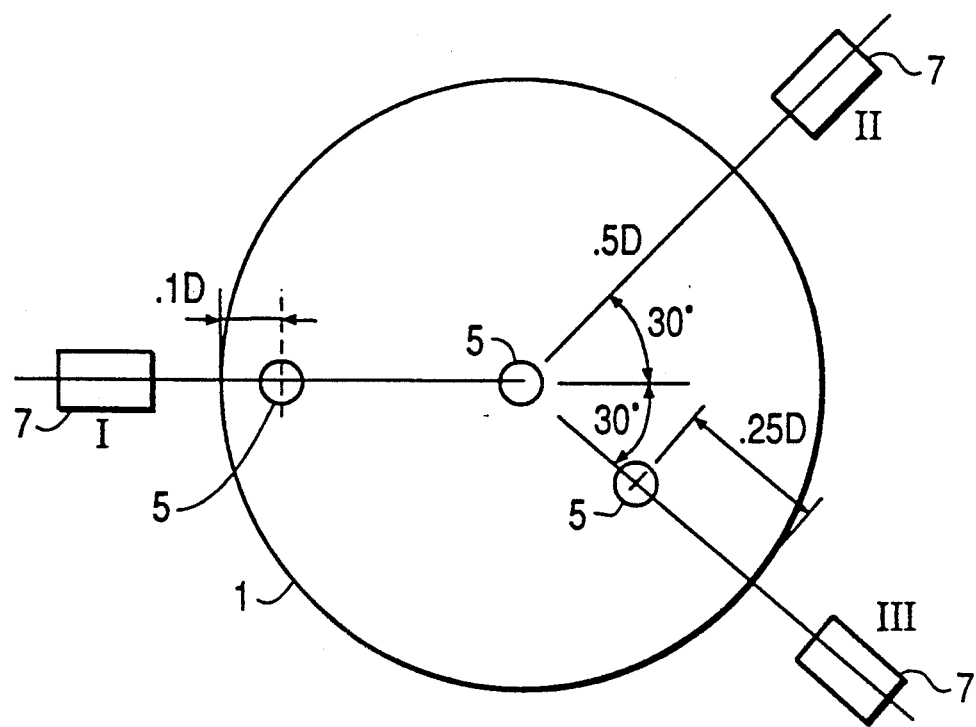

The sand distribution and the fluid flow pattern in a hydrocarbon flow are often unpredictable. Variations in the flow pattern also change the sand production and distribution in the pipe. It is therefore necessary with more than one specimen to monitor the total sand production. FIGS. 6A and 6B illustrate examples of optimal locations of three specimens or probes 5 in a pipe 1. These locations are optimal for a flow dominated either by liquid or gas. Specimens 5 and the detector 7 are located at three different levels, I, II, III as shown in FIG. 6A. The gaps between the different detectors were adequate to allow only one test specimen to send signals to one detector, i.e. a distance of 0.5–1 m between adjacent detectors. The tests showed that the locations of the specimen registered the total particle content in the above described flow. It will however always be necessary to have one specimen in the middle of the process flow and one or more laterally outwardly of the middle of the flow to cover and detect a non-uniform flow. The test specimens were mounted at angles of 45° to the process flow.

Test 3

Figure 7A:
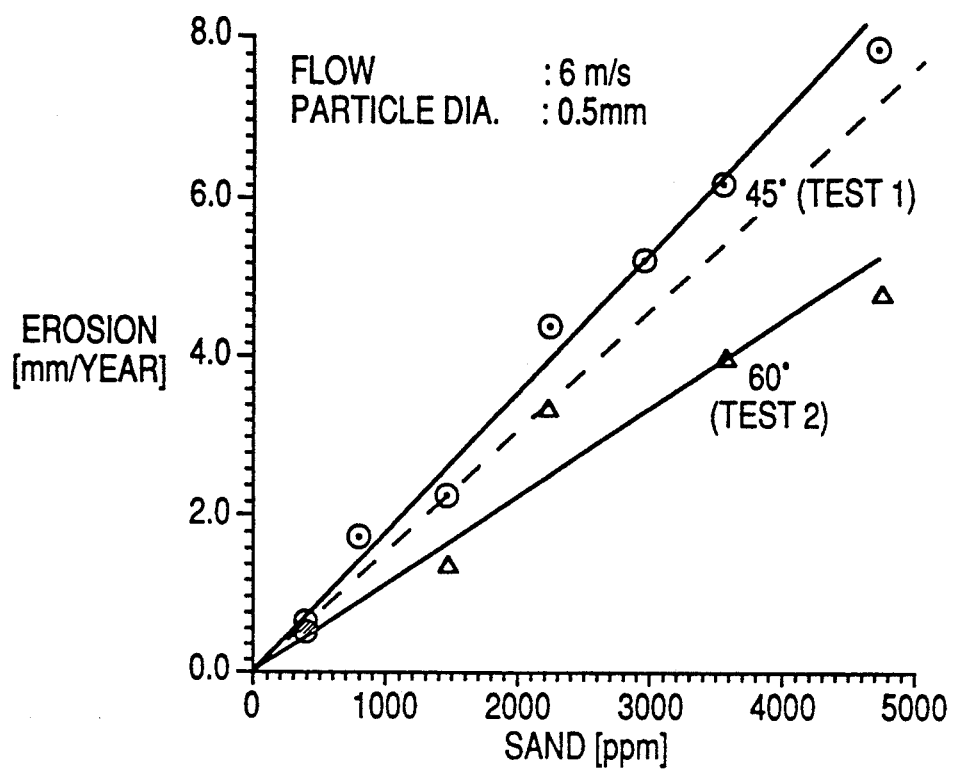
FIG. 7A is a graph showing the erosion velocity as a function of said concentration.

Tests were carried out to determine the effect of the sand concentration in the process flow. FIG. 7A illustrates the erosion velocity as a function of sand concentration when the angles of the test specimen to the process flow were 45° and 60°, and the fluid flow velocity 6 m/s. The grain size of the sand was 0.5 mm. As the graph illustrates, there is a linear correlation between the erosion velocity and the sane concentration. The scatter of some tests are due to tests taken from various test series. The dotted line represents calculated values.

Test 4

Figure 7B:
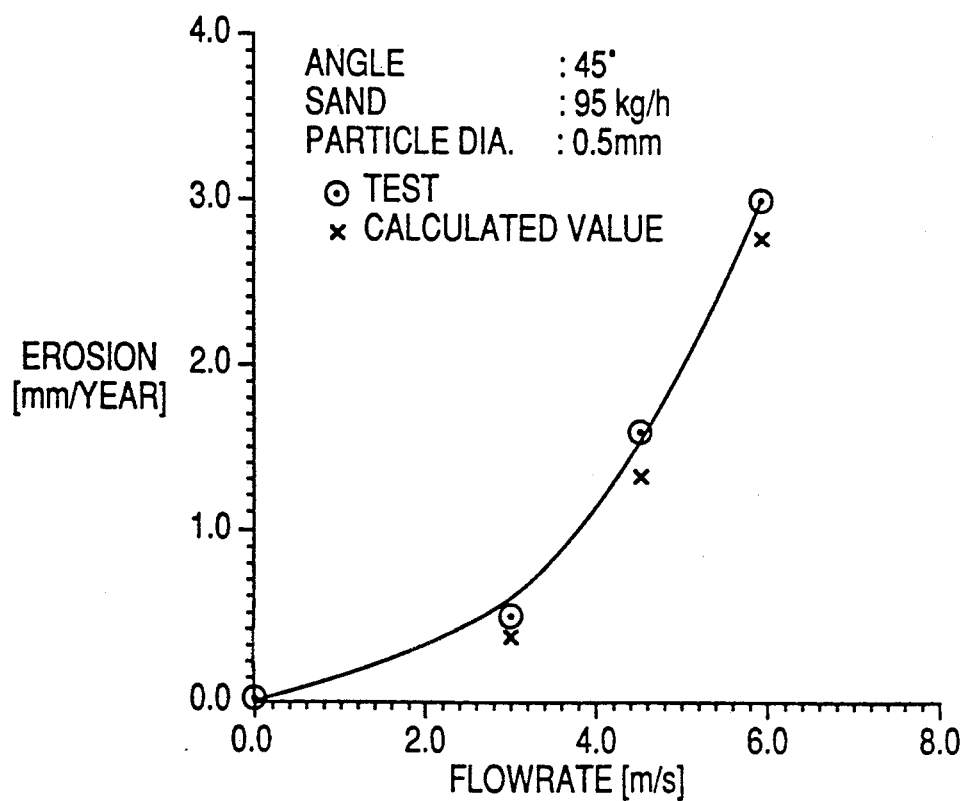
FIG. 7B is a graph illustrating the correlation between flow velocity and erosion velocity.

The effect of the flow velocity on the erosion velocity was determined. This is illustrated in FIG. 7B. The tests were carried out with a test specimen located at an angle of 45° to the flow, the sand concentration was 2000 ppm and the grain size of the sand was 500 μm. When the flow velocity increases, the sand concentration passing a section of the pipe increases proportionally. The erosion velocity measured at 3 m/s and 4.5 m/s was therefore corrected to represent the mass of sand equal to 95 kg/h passing the test specimen. The erosion velocity increases exponentially with the flow velocity, the Xs show the calculated erosion velocity when the velocity increases with a fluid flow velocity raised to the power of 2.3 (which is relatively common for sand in a gas flow).

Figure 8:
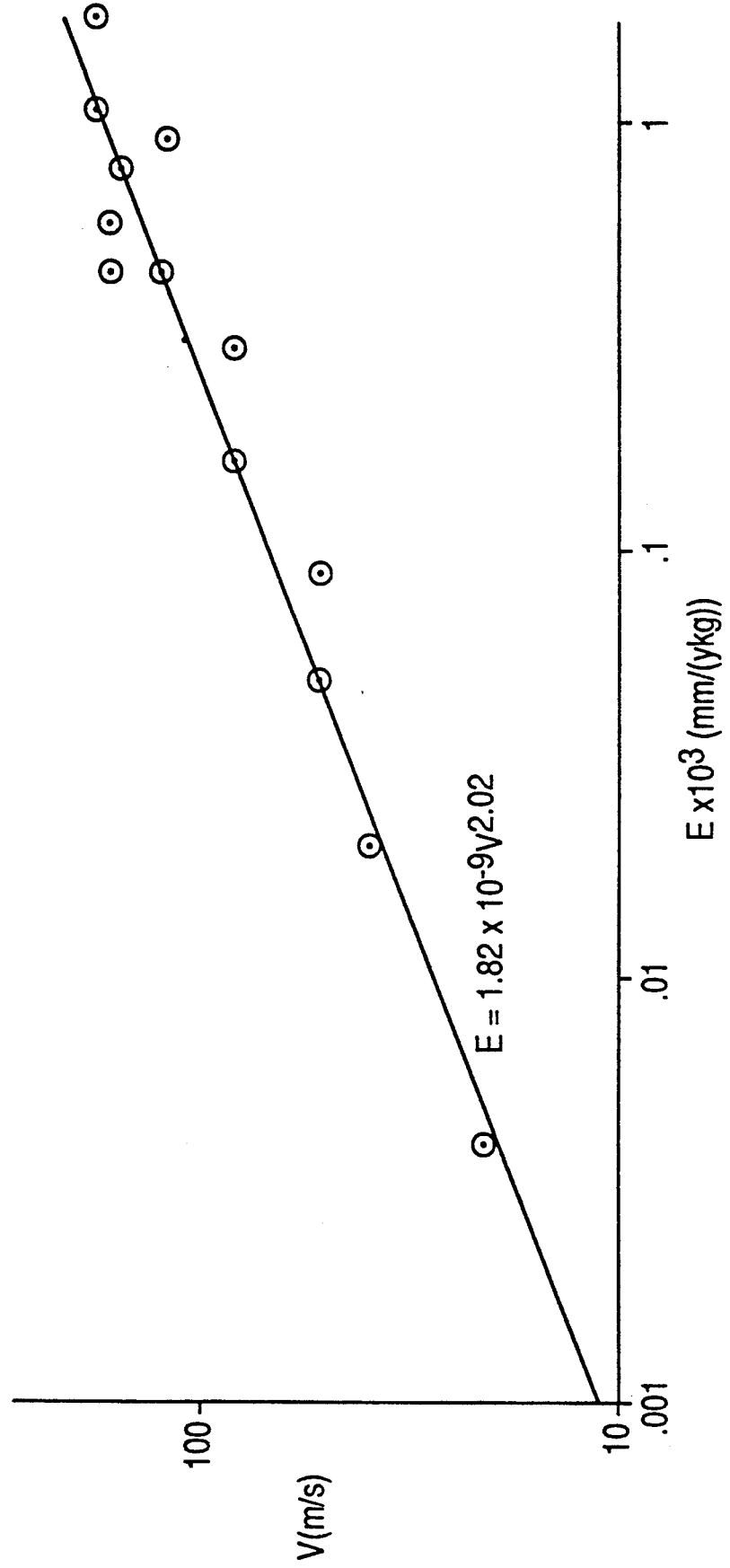
FIG. 8 is a graph showing the erosion velocity for steel as a function of the flow velocity for quartz particles in a flow of hydrocarbons.

The inventor also performed different tests in three phase flow (gas/liquid/sand flow) to find the relationship between the changes in the thickness of the test specimens or probes and the concentration of particles. The results were obtained by measuring the weight loss and using stationary ultra-sound probes. The literature reporting test results where erosion velocity is a function of flow velocity has been investigated for different steel qualities, particles and particle size in various environments. Erosion depends on the shape and hardness of the particle. From the reported data, 17 data were chosen for erosion on steel caused by semi-angular quartz sand with a distribution in size equal to sand produced in an oil/gas well. In FIG. 8 the data are plotted in a graph showing erosion velocity as a function of flow velocity. The results verify that there is a unique relation between change in thickness and sand concentration. The quantity of solid particles Mg (sand, etc.) which has impinged on a radioactive surface is given by:

$$Mg = \frac{E \times A}{K \times F \times V^{2.62}} \times (kg)$$

wherein
 E = Reduction of probe thickness (mm)
 A = The pipe cross sectional area (m$^2$)
 K = Material constant for the activated material
 F = Function of the flow density and mean diameter Dp (mm) of solid particles in the reservoir $$F = \frac{Dp}{B \times \phi^{0.5}}$$

B = Constant for all gas/liquid ratios
$\phi$ = Flow density (kg/m$^3$)

V = Velocity of the flow (m/s)

Calculated values are shown by the dotted lines in FIGS. 4 and 7.

The sand concentration can be calculated by registrating the material loss for the probes in the process flow. FIG. 9 shows the material loss during two hours at a sand concentration of 2300 ppm relative to the fluid flow. The test specimens had angles of 45° relative to the fluid flow, and the material loss was 1.05%. This is clearly indicated in the figure. Addition of 400 ppm sand for 6 hours also gave a clear indication as seen from FIG. 10. The loss of material was 0.5%. A material loss of 0.2% in 6 hours is also visible. The sensitivity of the equipment depends on how the data are sampled and analyzed. A material loss of 0.1% can be measured if the data are recorded and analyzed after the test. The data given in FIGS. 9 and 10 are not analyzed, but by using more sophisticated statistics the accuracy of the data analyzed can be improved and the time delay before the sand rate is detected can be further reduced.

It was found that without analyzing the signal, a reliable indication of sand production is at a 0.1% thickness reduction of the specimens, and the total sand concentration is confirmed upon reaching a 0.25% thickness reduction. By signal analyses the corresponding numbers are 0.05% and 0.1%. The accuracy of the system can be varied by changing the thickness of the activated specimens, very thin specimens giving a high level of accuracy. Specimens with different thicknesses can be used, depending on what length of life is desired for the specimens, and how important is a fast response regarding the particle content.

The method will detect sand production in a gas- or oil well in the following manner.

EXAMPLE 1

A gold specimen with cobalt was used as a gamma radiation source. The thickness of the specimen was 0.01 mm and it was mounted at an angle of 45° to the process flow. The following conditions shown in table 1 are for gas well;

TABLE 1

|  | Gas Well | |
|---|---|---|
|  | start production | last year production |
| Allowable sand production (kg/day) | 28 | 9 |
| Allowable fines production (kg/day) | 137 | 42 |
| Velocity well head (m/s) | 11 | 21 |
| Measured sand production after (hours) | 2.3 (3 kg) | 1.4 (0.8 kg) |
| Calculated particle production rate within (hours) | 6.3 (7 kg) | 3.5 (1.3 kg) |

The velocity in a gas well is high. Due to the danger of severe erosion in the well head, only low concentrations of sand are allowable. Sand production will be detected when only 0.5 to 2.5 kg sand has been produced.

EXAMPLE 2

The same type of test specimens as in Example 1 were used in an oil producing well having the following flow conditions as listed in table 2.

TABLE 2

| Oil Well | |
|---|---|
| Allowable sand production (kg/day): | 1351 (13% chrome steel) |
| Actual sand production (kg/day): | 742 |
| Velocity at well head (m/s): | 3.9 |
| Measured sand production after (hr): | 1.8 (99 kg) |
| Calculated particle production rate after (hr): | 4.5 (430 kg) |

The sand production in this well was 760 kg/day when the flow velocity Was 3.9 m/s (gas flux is 1.6 m$^3$/s/m$^2$). Because of the low production rate and gas/liquid ratio in this example it is difficult to detect sand for a detection system based on energy of the particles. However, by the method according to the invention it is possible to state that sand is produced after 2 hours of measurements and with a sand production of 100 kg. Total sand production can be calculated after 4.5 hours with an accumulated sand production of 430 kg. If further accuracy is required, the probes can be mounted in a pressure reducer (choke), provided that is a part of the process.

The tests illustrate that the system is independent of calibration. Even though the method according to the invention mainly has been described with regard to detection of sand in a hydrocarbon flow, it is suitable for detection of sand in other types of process flows where it is important to measure the concentration of abrasive particles. It is possible to detect particles as small as 0–0.5 mm in diameter. The sensitivity of the probes can be adjusted according to requirements, by selecting suitable thickness and material for the activated measuring element coated on the probe, measurements of sand concentration in oil wells (low sand particle energy) and gas wells (high sand particle energy) can be accomplished with required accuracy.

I claim:

1. A method for determining the content of particulate material in a fluid flow passing through a pipe, said method comprising:

positioning in said fluid flow within said pipe, at respective different positions across the internal cross section thereof, a plurality of probes each including radioactive material that is subject to being abraded by said particulate material in said fluid flow and that emits radiation that diminishes as a function of such abrasion;

positioning a plurality of radiation detectors outwardly of said pipe at locations such that each said detector detects radiation emitted only by a respective said probe;

detecting by said detectors radiation emitted from respective said probes; and determining the content of said particulate material in said fluid flow as a function of abrasion of said radioactive material of said probes based on the radiation detected by respective said probes.

2. A method as claimed in claim 1, comprising mounting said probes at an angle $\alpha$ relative to the direction of flow of said fluid flow, wherein $20° < \alpha < 60°$.

3. A method as claimed in claim 2, wherein $\alpha$ is approximately 45°.

4. A method as claimed in claim 1, comprising providing said probes as circular discs.

5. A method as claimed in claim 1, wherein said fluid flow comprises a hydrocarbon flow.

6. A method as claimed in claim 1, wherein said determining comprises calculating a concentration (Mg) of particulate material in said fluid flow according to:

$$Mg = \frac{E \times A}{K \times F \times V^{2.62}} \times (kg)$$

wherein:
 E = reduction of probe thickness (mm) due to abrasion
 A = cross sectional area (m²) of said pipe
 K = material constant for said radioactive material
 F = function of the flow density and mean diameter DP (mm) of said particulate material $$F = \frac{Dp}{B \times \phi^{0.5}}$$

B = constant for all gas/liquid (i.e. fluid) ratios
 φo = density (kg/m³) of fluid flow
 V = velocity of fluid flow (m/s).

7. A method as claimed in claim 1, comprising spacing said probes within said pipe.

8. A method as claimed in claim 7, comprising spacing said probes circumferentially within said pipe.

9. A method as claimed in claim 1, comprising spacing said probes circumferentially within said pipe.

* * * * *